United States Patent
Wu et al.

(10) Patent No.: US 7,213,445 B2
(45) Date of Patent: May 8, 2007

(54) ACOUSTIC PARTICULATES DENSITY SENSOR

(75) Inventors: Sean F. Wu, Troy, MI (US); Ravinder S. Beniwal, Harper Woods, MI (US)

(73) Assignee: Wayne State University, Detroit, MI (US)

( * ) Notice: Subject to any disclaimer, the term of this patent is extended or adjusted under 35 U.S.C. 154(b) by 35 days.

(21) Appl. No.: 10/948,617

(22) Filed: Sep. 23, 2004

(65) Prior Publication Data

US 2005/0076704 A1 Apr. 14, 2005

Related U.S. Application Data

(63) Continuation-in-part of application No. 10/308,868, filed on Dec. 2, 2002, now abandoned.

(60) Provisional application No. 60/338,409, filed on Dec. 5, 2001.

(51) Int. Cl.
*G01N 29/024* (2006.01)
(52) U.S. Cl. ..................... 73/24.03; 73/28.01
(58) Field of Classification Search .............. 73/24.03, 73/24.01, 28.01, 861.18, 861.23, 861.26
See application file for complete search history.

(56) References Cited

U.S. PATENT DOCUMENTS

| | | | |
|---|---|---|---|
| 3,710,615 A | 1/1973 | Johnson et al. | |
| 4,212,190 A | 7/1980 | Coover et al. | |
| 4,262,545 A * | 4/1981 | Lamarche et al. | ....... 73/861.27 |
| 4,445,389 A | 5/1984 | Potzick et al. | |
| 4,598,593 A | 7/1986 | Sheen et al. | |
| 4,718,269 A | 1/1988 | Der Kinderen | |
| 4,817,413 A | 4/1989 | Asano et al. | |
| 4,930,350 A | 6/1990 | Bode et al. | |
| 4,944,185 A | 7/1990 | Clark, Jr. et al. | |
| 5,060,514 A * | 10/1991 | Aylsworth | ................. 73/24.01 |
| 5,271,267 A | 12/1993 | Baumoel | |
| 5,313,820 A * | 5/1994 | Aylsworth | ................. 73/24.01 |
| 5,369,998 A * | 12/1994 | Sowerby | ................. 73/861.04 |
| 5,460,047 A | 10/1995 | Jacobson | |
| 5,467,637 A * | 11/1995 | Hasegawa et al. | ......... 73/24.01 |
| 5,616,872 A | 4/1997 | O'Brien | |
| 5,639,972 A | 6/1997 | Hastings et al. | |
| 5,831,150 A | 11/1998 | Sowerby et al. | |
| 5,886,264 A | 3/1999 | Hu et al. | |
| 5,907,099 A | 5/1999 | Huang | |
| 5,969,237 A | 10/1999 | Jones et al. | |
| 6,109,098 A | 8/2000 | Dukhin et al. | |

(Continued)

*Primary Examiner*—Hezron Williams
*Assistant Examiner*—Ryan Christensen
(74) *Attorney, Agent, or Firm*—Carlson, Gaskey & Olds, PC

(57) ABSTRACT

A technique for determining particulate density in a fluid monitors the changes in the speed of sound. Since the speed of sound is intimately related to the composites of the air mixture and since the speed of sound of clean air at any temperature and humidity can be calculated exactly, it is possible to estimate the density of any foreign particulates in the air by observing changes in the speed of sound. Formulations are derived that correlate the change in the speed of sound of the air mixture to their density fluctuations, thus allowing people to estimate the mass density of foreign particulates under any temperature and humidity. Alternatively, the change in density of the air mixture can be detected, thereby indicating the presence of contaminants and a possible alarm, even if the contaminants are not yet identified.

15 Claims, 3 Drawing Sheets

U.S. PATENT DOCUMENTS

| | | |
|---|---|---|
| 6,202,494 B1 * | 3/2001 | Riebel et al. ............ 73/861.29 |
| 6,227,040 B1 | 5/2001 | Hastings et al. |
| 6,405,603 B1 | 6/2002 | Baumoel |
| 6,435,030 B1 | 8/2002 | Gysling et al. |
| 6,446,494 B2 | 9/2002 | Hastings et al. |

* cited by examiner

ACOUSTIC PARTICULATES DENSITY SENSOR

RELATED APPLICATIONS

This application is a continuation-in-part of U.S. Ser. No. 10/308,868, filed Dec. 2, 2002 now abandoned, which claims priority to U.S. Provisional Ser. No. 60/338,409 filed Dec. 5, 2001.

BACKGROUND OF THE INVENTION

This invention provides a cost-effective methodology to measure the mass concentration of impurities in the air resulting from the exhaust of a combustion system such as diesel and gasoline engines used in the automotive industry. This methodology can also be used to measure any particulates in gas streams used in industry. It is drastically different from the conventional methods that are currently used by the automotive companies in monitoring particulates emissions. The invention can also be used to detect and/or identify and/or measure pollutants in ambient air.

Test data have shown that the average sizes of particulates from the exhaust of combustion systems are in the order of nanometers, or $10^{-9}$ meter, which are invisible but can be harmful when inhaled. The Environmental Protection Agency (EPA) has established strict regulations on the level of mass concentration of particulates discharged from the exhaust of combustion systems in order to reduce air pollution. The allowable level of particulates decreases every year as the demand on pollution control increases.

The conventional way of measuring the level of particulates concentration is to use a special filter to collect the residuals of the exhaust gases through a diluted chamber over certain period of time, and then weigh them on an electronic micro-scale inside a clean room. The equipment and facilities involved can be extremely expensive and the whole process can be very time consuming.

Quality of breathing air is an important health issue. While EPA has established outdoor air quality standards on ozone and particulates, no indoor air quality standards have been established except for the well known contaminants, such as Radon, as there are too many possible indoor air pollutants. Most people spend up to 90% of their time indoors. Although air contaminants in a private home may be limited to the owner's concern, air quality in office buildings, public transportations, theaters, stores, etc. is a public health issue. While it is possible that contaminated air in the outdoors manages to get inside a building, the source of air contamination is often found inside a building. Tobacco smoke, fungi, carbon monoxide, vapor from paint and carpet glue, and communication cables are well known sources of air pollution, but oftentimes the sensors are people who complain of nausea, headaches, red eyes, and dry mouths, many of which are dismissed as subjective sensations instead of serious illnesses. Thus, there is a need to be able to quantitatively detect the presence of various forms of air pollutants in a closed environment both timely and inexpensively. Such a sensor will be useful to locate the source of contaminations as well.

There are currently a number of airborne particle counters and toxin detectors available in the market, some of which are costly and require experienced operators.

SUMMARY OF THE INVENTION

The present invention monitors the change in the speed of sound in the gas being tested. Since the speed of sound is intimately related to the composites of the air mixture and since the speed of sound of clean air at any temperature and humidity can be calculated exactly, it is possible to estimate the density of any foreign particulates in the air by observing changes in the speed of sound. Formulations are derived that correlate the change in the speed of sound of the air mixture to their density fluctuations, thus allowing people to estimate the mass density of foreign particulates under any temperature and humidity. This new technique may include a function generator, power amplifier, speaker, humidity meter, thermometer, microphones, oscilloscope, and personal computer that are readily available in the market.

This new method is much simpler, more efficient and convenient, and costs much less than the existing technologies. Moreover, tests can be carried out on site and results can be printed out immediately.

Preliminary experiments have demonstrated that this technique is quite robust and sensitive. It can detect tiny little changes in the density fluctuations of airflow due to the presence of trace of smoke. The disadvantage of this new technique is that it cannot estimate the sizes of these foreign particulates. Rather, it yields an overall concentration level of particulates. On the other hand, the conventional methodology described above cannot measure the sizes of the particulates either.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF A PREFERRED EMBODIMENT

Figure 1:
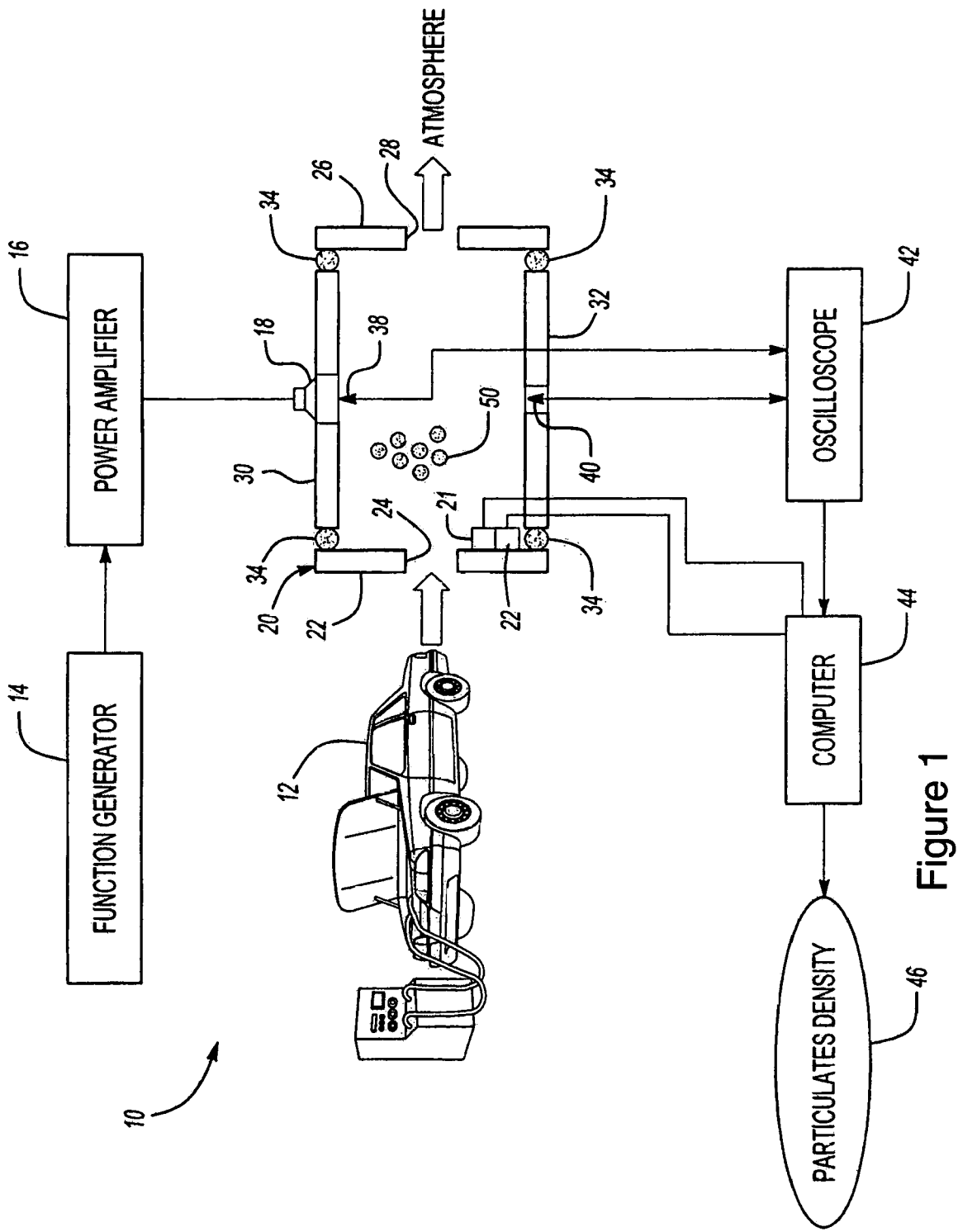
FIG. 1 is a schematic of the acoustic particulates density sensor of the present invention in use measuring particulates density from a vehicle exhaust.

FIG. 1 schematically illustrates the acoustic particulates density sensor 10 of the present invention in one potential use in measuring the particulate density of exhaust from a vehicle 12. The sensor 10 includes a function generator 14 which sends out an impulse that is amplified by a power amplifier 16. This impulse is emitted through a loudspeaker 18 mounted over an opening on a tube 20. An exhaust system of the vehicle 12 discharges a gas mixture through the tube 20 to atmosphere. A thermometer 21 and a humidity meter 22 measure the temperature and relative humidity of the airflow inside tube 20.

The tube 20 comprises a forward wall 22 having an opening 24 for receiving the exhaust gases and an opposing rearward wall 26 having an opening 28 for discharging the exhaust gases to atmosphere. The tube 20 further includes sidewalls 30 and 32 enclosing the tube 20 and connecting forward wall 22 to rearward wall 24. Foam 34 is disposed between the sidewalls 30, 32 and the forward and rearward walls 22, 26 to damp any vibration and prevent sound from being transmitted through the structure of the tube 20.

The impulse thus generated is measured by a microphone 38 on the same sidewall 30 as the speaker 18 and a microphone 40 mounted on the opposite sidewall 32. Signals from both microphones are received and displayed by an oscilloscope 42. The oscilloscope 42 sends these signals to a computer 44, which compares the arrival times of two signals to determine the time required for the signal to cross the tube 20. Since the distance across the tube 20 is fixed, the speed of sound through any gas mixture can be calculated. Note that calibrations must be done to determine the time required for the signal to travel across the tube 20 through pure air (i.e. without particulates). The microphone 38 can be used to cancel out ambient noise. If the molecular weight of the particulates is known, the computer 44 calculates the mass density of particulates 50 of the gas mixture and results are printed out at 46. Alternatively, the computer 44 may compare a change in the density to a threshold.

Figure 2:
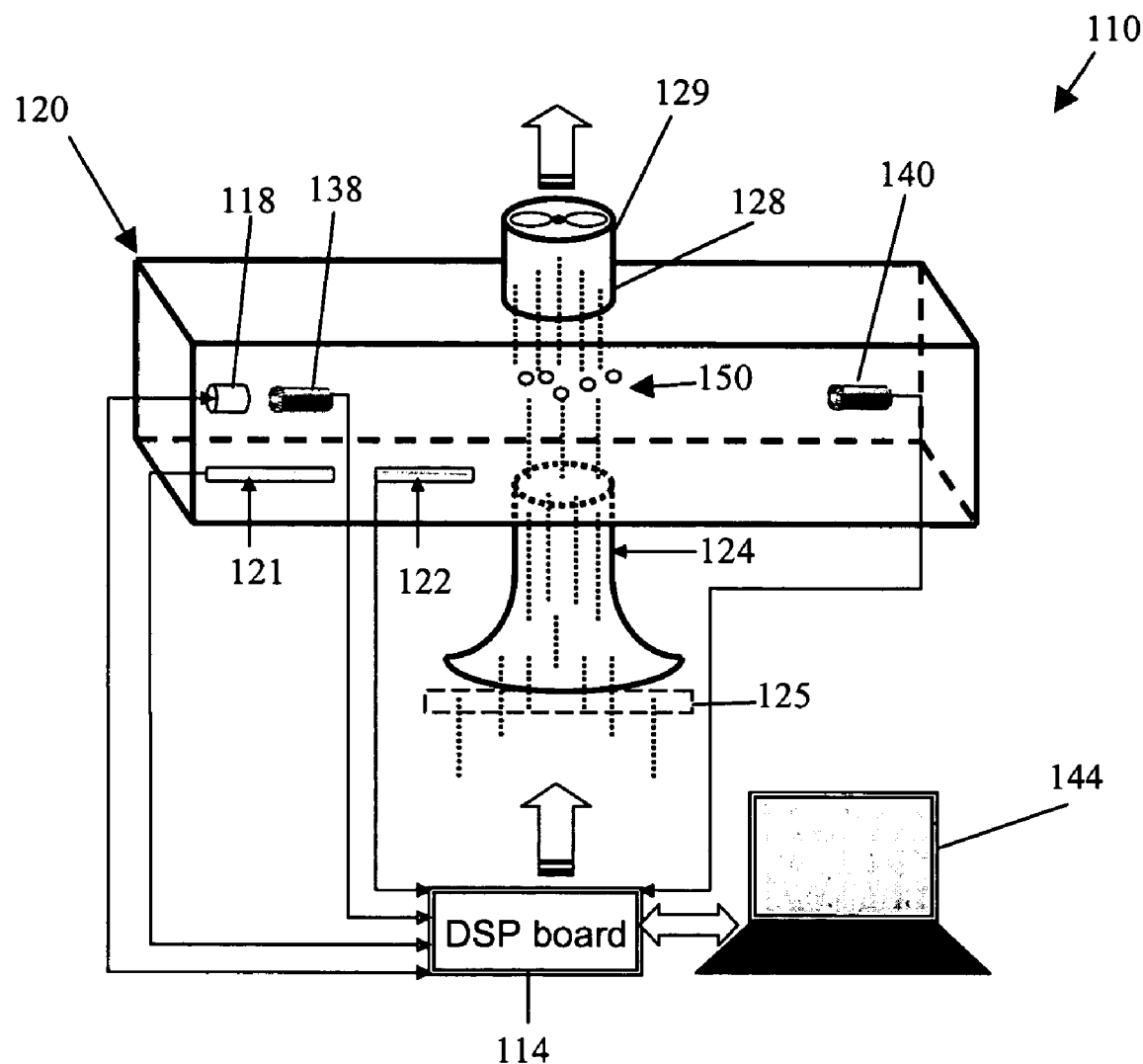
FIG. 2 is a schematic of the acoustic particulates density sensor of the present invention in use detecting and measuring particulates in ambient air.

FIG. 2 illustrates an acoustic particulates density sensor 110 according to a second embodiment of the present invention particularly for use in detecting and/or measuring contaminants in ambient air. The sensor 110 includes an ultrasonic emitter 118 mounted at one end of a plexiglass chamber 120. Microphones 138, 140 detect the traveling time t of pulses generated by the emitter 118. Any minute changes in t, after adjusting for ambient humidity and temperature as measured by the hygrometer 121 and thermometer 122 reflects a change in the air density. Therefore, by comparing the measured speed of sound with the calculated one in clean air under the same temperature and relative humidity, the presence of airborne impurities can be detected.

This sensor 110 is tested in a rectangular chamber 120 of dimensions m3. The microphones 138, 140, humidity sensor 122, temperature meter 121, and ultrasonic emitter 118 are off-the-shelf items. The signals from an ultrasonic emitter 118 are processed by a data signal processing board 114 in a PC that can generate impulses at fixed intervals, sample the data, convert analog signals to digital signal, and calculate the mass density. A complete cycle from sending out a signal to printing out the result takes less than a second.

In this embodiment, the ultrasonic emitter 118 and microphones 138, 140 are detached from the box to isolate vibration transmission from one element to another. The amplitudes of the 40 kHz pulses generated by the ultrasonic emitter 118 are amplified to enhance the S/N ratio. Pre- and post-processing techniques including smoothing, averaging, and curve fitting further enhance the S/N ratio. High sampling rates on ultrasonic signals will help ensure super-high resolution in the time delay measurements. In this embodiment, a small, low-speed fan 129 draws airflow into the chamber 120 so as to minimize the fluctuations in the ambient temperature and humidity.

Even if the molecular weights of airborne impurities are not given, this sensor 110 can still be used to detect their presence by comparing the measured sound speed of an air mixture with that of clean air under the same temperature and relative humidity. By comparing the change in speed (or density of the mixture) to a threshold, the presence of airborne impurities can be detected without knowing what the impurities are.

As an alternative, the sensor 110 could be used without an enclosure, i.e. without the chamber 120. When airborne impurities pass the line of traveling ultrasonic pulses, the speed of sound will deviate from that of clean air under the same conditions, and their presence will be detected. The downside of this alternative is that it may take longer to monitor airborne contaminants. To improve the efficiency, multiple sensors will be used to monitor airborne contaminants simultaneously.

Airborne contaminants can be loosely classified into different groups: e.g., gaseous vs. non-gaseous (aerosols), inorganic vs. organic, biological vs. non-biological, pathogenic vs. nonpathogenic, toxic vs. non-toxic, inert vs. corrosive. The sensor 110 could be used to construct a highly sensitive and effective sensor system that will discriminate all types of airborne contaminants. It is well known that HEPA (high efficiency particle air) filters can filter out 99.99% of the particles of diameters 0.3 μm or larger. They are used to eliminate allergens in conjunction with an activated charcoal filter. We will show that by adapting these filters the sensor 110 is capable of detecting and discriminating the targeted contaminants in a workplace.

Figure 3:
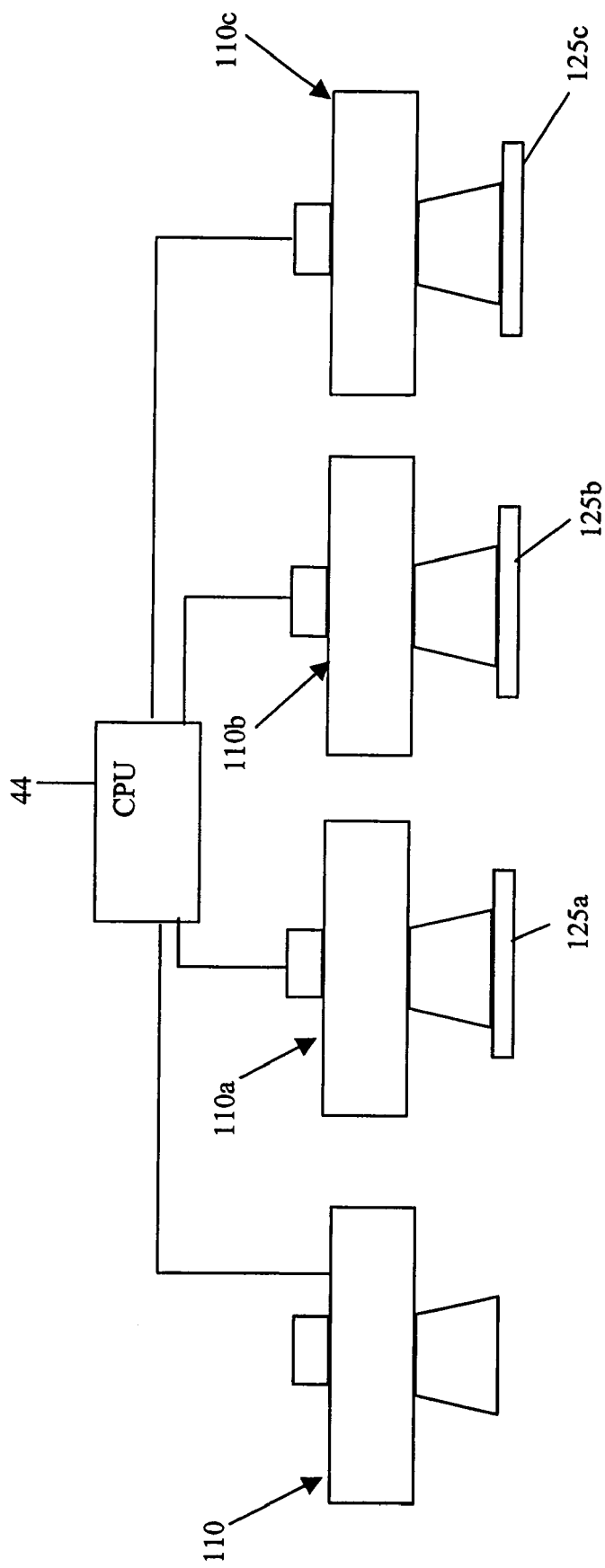
FIG. 3 illustrates an embodiment of the present invention with multiple sensors.

If an optional filter 125 is used, it can filter out particulates of a certain size (e.g. diameters 0.3 μm or larger) or it can filter out organic particulates, or both. In that way, as shown in FIG. 3, two or more sensors 110, 110a, 110b, 110c can be used together, each having a different filter 125a–c or no filter. The differences in the measurements by the different sensors 110, 110a–c, can be used by the computer 44 to identify the particulates.

For all of the embodiments described with respect to FIGS. 1–3, the mathematical model that correlates any change in the speed of sound of an air mixture to density fluctuations will be discussed below. According to Laplace's adiabatic assumption for an ideal gas, the speed of sound can be expressed in general as $$c = \sqrt{\gamma RT}, \quad (1)$$

where $\gamma$ is the specific heat ratio, T is absolute temperature, and $R = R_0/M$, here $R_0 = 8314$ (J/kg K) is a universal gas constant, and M is the average molecular weight of the gas.

Equation (1) indicates that any change in the average molecular weight of gas will result in changes in the speed of sound, provided that the temperature T remains constant. If we denote $d_{imp}$ as the density of impurities, we can relate it to the average molecular weights of the air by [13]

$$d_{imp} = \left[\frac{\alpha_{imp}(1+\alpha_{wet})W_{air}}{(1+\alpha_{wet})W_{air} - W_{imp}}\right]\left(\frac{W_{imp}}{V}\right). \quad (2)$$

In this equation V is the molar volume of air mixture, $$V = \frac{(273.16+T) \times 22.4 \times 0.001}{273.16} = 8.2 \times 10^{-4}(273.16+T), \quad (3)$$

where T is temperature in Celsius, $W_{air} = 29$ is the average molecular weight of dry air, $W_{imp}$ represents the average molecular weight of impurities, and $\alpha_{wet}$ and $\alpha_{imp}$ stand for the ratios of speeds of sound caused by relative humidity and presence of impurities in the air, respectively, $$\alpha_{wet} = \left(\frac{\gamma_{wet}}{\gamma_{dry}}\right)\left(\frac{331+0.61T}{C_{wet}}\right)^2 - 1 \text{ and } \alpha_{imp} = \left(\frac{C_{wet}}{C_{meas}}\right)^2 - 1. \quad (4)$$

Here $\gamma_{dry}$ and $\gamma_{wet}$ are the specific heat ratios of dry and wet air, respectively, $$\gamma_{dry} = 1.4 \text{ and } \gamma_{wet} = (7+M_{wet})/(5+M_{wet}), \quad (5)$$

and $C_{wet}$ and $C_{meas}$ are the sound speed of the humid air and measured speed of sound, respectively, $$C_{wet}=(331+0.61T)\times[1+0.16\times P(T)/10132500]$$

and $C_{meas}=0.235\times 10^6/t-198$, (6)

where t is the measured time. The quantity $M_{wet}$ in Eq. (5) is the mole fraction of water in the air and is given by, $$M_{wet}=h\times P(T)/10132500, \quad (7)$$

where h is the relative humidity in the air and P(T) is the saturated pressure that can be written as a function of temperature T as $$P(T)=10^6\times e^{F(T)}. \quad (8)$$

The exponent F(T) is given by [14]

$$F(T) = 10.459 - 4.04897\times 10^{-3}T - 4.1752\times 10^{-5}T^2 + \quad (9)$$
$$3.6851\times 10^{-7}T^3 - 1.0152\times 10^{-9}T^4 + 8.6531\times 10^{-13}T^5 +$$
$$9.03668\times 10^{-16}T^6 - 1.9969\times 10^{-18}T^7 + 7.79287\times 10^{-22}T^8 +$$
$$1.91482\times 10^{-25}T^9 - 3968.06/(T - 39.5735)$$

These formulations show that given the average molecular weight $W_{imp}$, temperature T, relative humidity h, and time delay t, we can calculate the density of impurities in any airflow.

As an example, Eq. (2) is used to estimate the mass density of a trace of incense smoke flowing into the chamber (see FIG. 1). The temperature and relative humidity are 24.8° C. and 46.8, respectively. The major constituent of molecules of smoke is carbon, $W_{imp}$=12, and the time delay between two microphones is t=875 µs. The saturated pressure P(T)=3136.42 Pa, the mole fraction of water $M_{wet}$=0.01449, the specific heat ratio of wet air $\gamma_{wet}$=1.398844427, the sound speed in humid air $C_{wet}$=346.93 m/s, the measured sound speed $C_{meas}$=347.12 m/s, the values $\alpha_{wet}$=-0.005441211 and $\alpha_{imp}$=-0.001090829, the molar volume of air mixture V=0.02443368, and the average molecular weight of the air $W_{av}$=28.84220488. Substituting these values in Eq. (2) yields $d_{imp}$=0.9174 g/m³, which is the density of carbon due to incense smoke in the chamber.

Next, all conditions remain unchanged but the amount of smoke is increased just a little such that the time delay increases to t=874.999 µs, namely, a mere nanosecond difference. The density of carbon molecules in the chamber becomes $d_{imp}$=0.920 g/m³.

These results indicate that this sensor is sensitive enough to detect changes of 0.0026 g/m³ or 2.0 ppm of carbon in the air. Since these formulas are valid for any temperature and relative humidity, it can be utilized to monitor changes in airborne impurities in real time.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope. Alphanumeric identifiers for steps in the method claims are for ease of reference by dependent claims, and do not indicate a required sequence, unless otherwise indicated.

What is claimed is:

1. A method for measuring particulates density in air including the step of steps of:
   measuring a speed of a sound wave through the air; and
   determining the particulates density in the air based upon the speed of sound wave through the air by correlating the changes in sound speeds to the density of the contaminant $d_{imp}$ as the density of impurities, and the average molecular weights of the air by $$d_{imp} = \left[\frac{\alpha_{imp}(1 + \alpha_{wet})W_{air}}{(1 + \alpha_{wet})W_{air} - W_{imp}}\right]\left(\frac{W_{imp}}{V}\right)$$

where V is the molar volume of air mixture, $W_{air}$ is the average molecular weight of dry air, $W_{imp}$ represents the average molecular weight of impurities, and $\alpha_{wet}$ and $\alpha_{imp}$ stand for the ratios of speeds of sound caused by relative humidity and presence of impurities in the air, respectively.

2. A method for detecting contaminants in air including the steps of:
   generating a sound wave;
   sensing the sound wave;
   measuring change in the speed of the sound wave propagating through the air based upon the sensing of the sound wave and based upon the sensing of the sound wave and based upon relative humidity of the air through which the sound wave passed; and
   detecting contaminants in the air based upon a change in the speed of sound wave through the air by correlating the changes in sound speeds to the density of the contaminant $d_{imp}$ as the density of impurities and the average molecular weights of the air by $$d_{imp} = \left[\frac{\alpha_{imp}(1 + \alpha_{wet})W_{air}}{(1 + \alpha_{wet})W_{air} - W_{imp}}\right]\left(\frac{W_{imp}}{V}\right)$$

where V is the molar volume of air mixture, $W_{air}$ is the average molecular weight of dry air, $W_{imp}$ represents the average molecular weight of impurities, and $\alpha_{wet}$ and $\alpha_{imp}$ stand for the ratios of speeds of sound caused by relative humidity and presence of impurities in the air, respectively.

3. The method of claim 2 further including the step of generating the sound wave at one end of an enclosure.

4. The method of claim 3 further including the step of sensing the sound wave at an opposite end opposite the one end of the enclosure.

5. The method of claim 4 further including the step of measuring a time for the sound wave to travel through the air from the one end to the opposite end of the enclosure.

6. The method of claim 5 further including the steps of:
   sensing the sound wave at the one end; and
   determining the speed of the sound wave through the air based upon the step of sensing the sound wave at the one end and based upon the step of sensing the sound wave at the opposite end.

7. The method of claim 6 further including the step of comparing the sound wave sensed at the one end to the sound wave sensed at the opposite end to determine the time of travel.

8. The method of claim 7 further including the step of drawing air through the enclosure.

9. An acoustic particulates density sensor comprising:
   an at least partially enclosed container;
   a first transducer for generating a sound wave in the container;

a second transducer for sensing the sound wave in the container;

a meter for measuring humidity inside the container; and a computer for determining a time of travel of the sound wave in the container and detecting a presence of contaminants in the air based upon the time of travel of the wave and the humidity inside the container, wherein the computer determines a density of contaminants in the air based upon the speed of sound through the air by correlating the changes in sound speeds to the density of the contaminant $d_{imp}$ as the density of impurities and the average molecular weights of the air by $$d_{imp} = \left[\frac{\alpha_{imp}(1 + \alpha_{wet})W_{air}}{(1 + \alpha_{wet})W_{air} - W_{imp}}\right]\left(\frac{W_{imp}}{V}\right)$$

where V is the molar volume of air mixture, $W_{air}$ is the average molecular weight of dry air, $W_{air}$ represents the average molecular weight of impurities, and $\alpha_{wet}$ and $\alpha_{imp}$ stand for the ratios of speeds of sound caused by relative humidity and presence of impurities in the air, respectively.

10. The acoustic particulates density sensor of claim 9 further including a third transducer between the first transducer and the second transducer, the computer determining the time of travel of the sound wave from the third transducer to the second transducer.

11. The acoustic particulates density sensor of claim 10 wherein the wave is a sound wave.

12. The acoustic particulates density sensor of claim 11 wherein the sound wave is an impulse.

13. The acoustic particulates density sensor farther of claim 12 wherein the first transducer is a loudspeaker.

14. The acoustic particulates density sensor of claim 13 wherein the second and third transducers are microphones.

15. The acoustic particulates density sensor of claim 9 farther including a fan drawing air through the container.

* * * * *

UNITED STATES PATENT AND TRADEMARK OFFICE
CERTIFICATE OF CORRECTION

PATENT NO. : 7,213,445 B2
APPLICATION NO. : 10/948617
DATED : May 8, 2007
INVENTOR(S) : Wu et al.

It is certified that error appears in the above-identified patent and that said Letters Patent is hereby corrected as shown below:

Claim 9, Column 7, line 20: "$W_{air}$" should be --$W_{imp}$--

Claim 13, Column 8, line 13: Delete "farther"

Signed and Sealed this

Tenth Day of July, 2007

JON W. DUDAS
*Director of the United States Patent and Trademark Office*